(12) United States Patent
Dyer

(10) Patent No.: US 12,194,073 B1
(45) Date of Patent: Jan. 14, 2025

(54) METHOD OF ARTHROPOD EGRESS

(71) Applicant: Gordon W. Dyer, Hobbs, NM (US)

(72) Inventor: Gordon W. Dyer, Hobbs, NM (US)

( * ) Notice: Subject to any disclaimer, the term of this patent is extended or adjusted under 35 U.S.C. 154(b) by 0 days.

(21) Appl. No.: 18/445,610

(22) Filed: Nov. 17, 2023

(51) Int. Cl.
*A61K 36/61* (2006.01)
*A61K 47/36* (2006.01)
*A61K 47/44* (2017.01)

(52) U.S. Cl.
CPC .............. *A61K 36/61* (2013.01); *A61K 47/36* (2013.01); *A61K 47/44* (2013.01)

(58) Field of Classification Search
CPC ......... A61K 36/61; A61K 47/36; A61K 47/44
See application file for complete search history.

(56) References Cited

U.S. PATENT DOCUMENTS

| | | | |
|---|---|---|---|
| 11,457,626 B2 | 10/2022 | Dyer | |
| 2011/0319341 A1* | 12/2011 | Awada | A01N 63/22 514/23 |
| 2020/0022934 A1* | 1/2020 | Mathur | A61K 9/124 |

OTHER PUBLICATIONS

U.S. Appl. No. 18/088,347, filed Jul. 6, 2023, Sight Sciences, Inc.

* cited by examiner

*Primary Examiner* — Robert A Wax
*Assistant Examiner* — Quanglong N Truong

(57) ABSTRACT

This invention provides a way for drugs to kill a wide variety of otherwise invulnerable arthropods, which are protected by an unwettable plastron shield that encoats their bodies, by providing the drug with a means of egress through this plastron. Also, many arthropod-related diseases are caused by a combination of underlying factors, not just the mite. This invention allows for the concomitant use of other, non-mite-related, lipophilic drugs. This "combo" drug approach potentially allows for the treatment of the all of factors causing the disease at the same time.

14 Claims, No Drawings

METHOD OF ARTHROPOD EGRESS

FIELD OF THE INVENTION

The present invention relates to the use of low molecular weight non-polar (LMWNP) chemicals to aid in the penetration of anti-parasitical medicaments through the unwettable plastron shield protecting certain arthropods, and thereby better enable these agents to kill the arthropod. More particularly, the present invention teaches the use of LMWNP excipients to act enhance the ability of pharmaceutical agents kill *Acari, Heteroptera*, and *Anoplura* arthropods.

DESCRIPTION OF RELATED ART

*Demodex* mites are obligate parasites that chronically infest the eyelid follicles and meibomian (tear-oil producing) glands of all humans have plastrons that encoat and protect these mites by making their bodies unwettable. In addition to causing a significant form of blepharitis, the chronic, infestation-related damage that they do to these meibomian oil glands is thought to be the main cause of Dry Eye Disease (also known as Meibomian Gland Dysfunction) in middle-aged and older patients due to not having sufficient tear oil to seal in the moisture of the tears (Jingbo Liu, Hosam Sheh, Scheffer C. G. Tseng, Pathogenic role of *Demodex* mites in blepharitis. Curr Opin Allergy Clin Immunol. 2010 October; 10(5): 505-510). Further, as is well known, such plastron-protected arthropods also play a roll in head lice infestation, bed bugs, tick infestation, scabies, and acne rosacea. What is less well known is that plastron-protected mites, rather than just fungi, also play a role in Athlete's Foot disease (Adamczyk K, Garncarczyk A, Antończak P, Wcisło-Dziadecka D. The Foot Microbiome. J Cosmet Dermatol. 2020 May; 19 (5): 1039-1043. doi: 10.1111/jocd.13368. Epub 2020 Mar. 11. PMID: 32162464).

Currently known medicament/medicaments used to kill plastron-bearing arthropods include: crotamiton, benzylbenzoate (benzoates generally), Ivermectin (avermectins generally), lindane, permethrin (pyrethroids generally), azithromycin azelaic acid, and anilides.

Soon to issue U.S. patent application Ser. No. 18/088,347, Formulations And Methods For Treating Conditions Of The Eye, similarly to the teachings of my (U.S. Pat. No. 11,457, 626 B2, Col. 2, line 27 and Abstract) claims the use of medicaments, namely azithromycin, avermectins (a group that includes the well known ivermectin, long used for killing mites) and dicarboxylic acids, similarly to my (U.S. Pat. No. 11,457,626 B2) invention's preferred dicarboxylic acid embodiment, to kill mites. Although Formulations And Methods For Treating Conditions Of The Eye does not directly address the benefit of using LMWNP excipients as does my (U.S. Pat. No. 11,457,626 B2) invention, it teaches to use excipient formulations that, except for gels, are all non-polar (cream, oily solution, ointment, oily spray, mineral oil, petrolatum, or skin penetration enhancer, ¶187, ¶193), all of presumptively LMWNP nature particularly the oils, and therefore inherently harmful to the mites that cause dry eye disease, as already taught by my (U.S. Pat. No. 11,457,626 B2) invention. Finally, Formulations And Methods For Treating Conditions Of The Eye fails to point out that the reason that dicarboxylic acids work at killing mites is that, as calcium chelators (see above), they naturally attack the calcium located at the base of each plastron unit, again, as already taught by my invention (U.S. Pat. No. 11,457,626 B2).

There are currently no FDA approved treatments for blepharitis, and there are only four FDA approved drugs (Restasis®, Xiidra®, Cequa®, and Eysuvis®) for treating dry eye, which all act to reduce inflammatory aspects of the condition. In cases where bacterial infection results, topical or oral antibiotics may be administered, although these might not treat the underlying cause of the disease, and chronic use can result in undesired toxicity or side effects. Available treatment strategies are therefore largely palliative, the such as the use of artificial tears such as Miebo™ (perfluorohexyloctane) and maintaining proper lid hygiene. Eyelid warming using warm compresses is the standard eyelid therapy to increase meibum fluidity in patients with obstructed meibomian glands, but warm compresses are inexact and often ineffective (i.e., are too hot, are not hot enough for long enough, cool off too fast to do so effectively, do not conform to the eyelids sufficiently enough to achieve requisite sufficiently elevated meibum melting temperatures), compliance is an issue, and chronic use can result in thermal injury to ocular tissue. Opening of obstructed meibomian glands by physical expression or lid massage can improve secretion and dry eye symptoms, but compliance remains an issue as with warm compresses, the necessary procedures can cause damage to sensitive tissues (e.g., undesirable corneal remodeling from rubbing the eyelids and applying undesirable pressure on the cornea), and the therapeutic effects are short-lived.

In view of the foregoing, it would be desirable to enhance the ability of medicaments/medicaments to kill the plastron-bearing arthropods that, at least in part, cause the above diseases, including blephartis, by using a LMWNP excipient to carry these medicaments through the plastron and thus onto/into the arthropod. This is particularly desirable if it is a parasitic arthropod present in/on delicate human or honey bee tissue where the unenhanced effective treatment dosages of these medicaments might be toxic to the host. It would further be desirable, because of the LMWNP solubility of many ancillary medicaments (see below Table 1), such as cyclosporin which is used in the treatment of Dry Eye Disease or anti-fungals used in the treatment of Athlete's Foot disease, to act as an excipient for these complementary disease treatment medicaments.

DESCRIPTION OF THE INVENTION

As mentioned above, plastrons are a cuticular bubble of air that protects many arthropods from direct contact with their external environment by making them unwettable, a Cassie-Baxter physical state. The generalized organization of this plastron-bearing cuticle formation is that of a multitude of microscopic lipid-bearing (esters, steroids and monocyclic terpenes) 'trees' each surrounded by a protein-rich 'grass', all growing out of and supported by a 'soil' of multiple layers of chitin and hardened with calcium, resulting in an unwettable Cassie-Baxter physical state within the narrowly segmented 'cells' of the plastron (Roy A. Norton, Valerie M. Behan-Pelletier, Calcium carbonate and calcium oxalate as cuticular hardening agents in oribatid mites. Canadian Journal of Zoology, 1991, 69 (6): 1504-1511). Possibly because such an unwettable state is so difficult to achieve, there is surprisingly little variation in the makeup of each unwettable plastron unit ('cell') from species to species, even when comparing the arthropod plastrons to plant plastrons (Song Ha Nguyen, Hayden K. Webb, Peter J. Mahon, Russell J. Crawford and Elena P. Ivanova, Natural Insect and Plant Micro-/Nanostructsured Surfaces: An Excellent Selection of Valuable Templates with Superhydrophobic and Self-Cleaning Properties. Molecules 2014, 19 (9), 13614-13630).

The determinant of whether a chemical or mixture of chemicals will penetrate a plastron, whether the chemical is a simple alkane, a semi-fluorinated alkane, a terpene, a dimethicone, or mixture of any of these chemicals encompassed by the present invention, is its Laplace pressure and, due to Cassie-Baxter physical state math, its molecular size rather than the particular name and class of the chemical. The chemical will penetrate the plastron if it is sufficiently LMWNP enough to breach and the normally unwettable, (Cassie-Baxter state) plastron surface, as detailed below:

the Laplace Pressure equation states:

$$\Delta p = \gamma(1/R_x + 1/R_y)$$

where:

$\Delta p$ is the gas/liquid boundary pressure difference, known as the Laplace pressure.

$\gamma$ is surface tension.

$R_x$ and $R_y$ are radii of curvature in each of the axes that are parallel to the surface.

For an arthropod, given the small size of each compartmental plastron unit, the slight difference between the two radii of curvature is irrelevant and thus the key to understanding the implication of the above equation is that small size (and hence small radius) arthropod plastron units have surprisingly high internal Laplace pressure resistance against the incursion of a polar liquids because of their high surface tension (y) value but, conversely, arthropod plastron units have limited internal Laplace pressure resistance against the incursion of a non-polar liquids, especially when the molecule is small (see below), even with small radii of curvature, because of their low surface tension (y) value. Further, a special, fortuitous situation arises when, as is the case for an arthropod plastron, air is the internal gas used in generating the Laplace pressure because then the Cassie-Baxter equation for calculating the minimum required wetting angle of any LMWNP solution not to breach and (and thus wet/touch) the plastron unit surface of the arthropod simplifies to:

$$\cos \theta_{cb} = \sigma_1 \cos \theta - \sigma_2$$

where:

$\cos \theta_{cb}$ is the necessary Cassie-Baxter state wetting angle required to be assumed by the liquid to maintain an unwettable relationship relative to air-filled valleys of the underlying solid.

$\cos \theta$ is the angle that the liquid assumes where it touches the mountain peaks of the underlying solid.

$\sigma_1$ and $\sigma_2$ are the surface areas of mountain peaks and air-filled valleys of the arthropod plastron unit in contact with the overlying liquid, respectively.

Therefore, an arthropod plastron, though robust against larger molecular weight non-polar solutions, is inherently vulnerable against a sufficiently LMWNP solution whether this solution is an alkane, a semi-fluorinated alkane, a dimethicone, a terpene, or some other LMWNP chemical. In addition, as explained above, wetting angles are measurable, as is the exact size and structural arrangement of the particular arthropods's plastron unit, although there is little variation in plastron units even between different species, and thus the person of ordinary skill in the art is enabled to use this invention with only minor experimentation. Further, this inherent plastron limitation means that any chemical substance dissolved in, emulsified in, or colloidally suspended within the sufficiently LMWNP excipient will be carried along from this external environment onto/into the arthropod when the plastron's Laplace pressure protecting the arthropod is overcome/pierced/passed through/penetrated by this LMWNP excipient (Thierry Darmanin, Frédéric Guittard, Superhydrophobic and superoleophobic properties in nature. Materials Today, Volume 18, Issue 5, June 2015, Pages 273-285).

"The solubility data indicate that ivermectin has the highest solubility in tea tree oil followed by ethylbutanoate among the oils tested." Surajit Das et al, Development of microemulsion based topical ivermectin formulations: Preformulation and formulation studies. Colloids and Surfaces B: Biointerfaces, Volume 189 May 2020, 110823; https://doi.org/10.1016/j.colsurfb.2020.110823

Michael Marks et al, Randomized Trial of Community Treatment With Azithromycin and Ivermectin Mass Drug Administration for Control of Scabies and Impetigo, Clinical Infectious Diseases, Volume 68, Issue 6, 15 Mar. 2019, Pages 927-933.

"The present study's results revealed that all three concentrations of azelaic acid had anti-*Demodex* efficacy comparable to that of 5% permethrin." Botsali A., Yürekli A. Comparison of the in vitro *Demodex folliculorum* killing activity of azelaic acid and permethrin. J Health Sci Med/JHSM. 2022; 5 (2): 558-563.

"Dicarboxylic acids bind divalent metals, particularly calcium. Azelaic acid is an amphiphilic dicarboxylic acid." Litvinov D et al., Anti-atherosclerotic actions of azelaic acid, an end product of linoleic acid peroxidation, in mice. Atherosclerosis. 2010 April; 209 (2): 449-54. doi: 10.1016/j.atherosclerosis.2009.09.076. Epub 2009 Oct. 12. PMID: 19880116; PMCID: PMC2846213.

"People with scabies infection are at increased risk for impetigo." Centers for Disease Control and Prevention; https://www.cdc.gov/groupastrep/diseases-public/impetigo.html.

"*Demodex* mites carry bacteria, like 'Staphylococcus aureus', that can trigger inflammation that leads to blepharitis." Blepharitis and the mites that live on your eyelids | Glaucoma UK; https://glaucoma.uk/blog; 8 Nov. 2022.

"(T)ea tree oil cream, applied twice daily for one month, has been shown to be effective in relieving symptoms of athlete's foot." https://www.mayoclinic.org/drugs-supplements-tea-tree-oil.

Fabrizi V, Zacconi I, Principato M, Pesca C, Cruciani D, Crotti S, Papini M. Toenail onychomycosis by *Trichophyton rubrum* and concurrent infestation with Tyrophagus putrescentiae. Infez Med. 2017 Dec. 1; 25 (4): 377-380. PMID: 29286021.

The foregoing description is intended to be illustrative and is not to be taken as limiting. Other variations within the spirit and scope of this invention are possible and will be apparent to those skilled in the art.

TABLE 1

Non-aqueous vehicles used in ocular drug delivery systems.

| Drug (Tradename) | Vehicle | Study outcome | Ref. |
|---|---|---|---|
| Solutions | | | |
| Pilocarpine | Castor oil | Drug accumulation in superficial corneal and conjunctival cells | [105] |
| Ataluren | DMSO and castor oil | Sterility maintained and drug degradation inhibited; no penetration studies performed | [78] |
| Cyclosporine A | Olive or castor oil | Clinically relevant therapeutic responses observed in DED; poor ocular bioavailability in comparison to oral dose in uveitis patients | [106], [107], [108], [109] |
| Pimecrolimus | Corn oil | Better clinical outcomes and safety than ointments in dogs with DED | [110] |
| Azithromycin Azyter ® | MCT | Significant improvement in clinical efficacy in bacterial or trachomatous conjunctivitis in comparison to systemic administration; relatively well tolerated; mild to moderate adverse events (if any) in clinical trials; currently marketed in Europe for bacterial conjunctivitis | [111], [112] |
| Cyclosporine A CyclASol ® | SFA (F4H5) | Significant improvement in ocular bioavailability and clinical efficacy; good tolerability; safety and efficacy confirmed in Phase II and III clinical trials | [16], [113] |
| Tacrolimus | SFA (F4H5) | Significant improvement in clinical signs of uveitis; greater intraocular penetration than aqueous suspension; patent pending (WO2018114557 A1) | [114] |
| Latanoprost | SFA (F4H5, F6H8) | Clinical efficacy comparable to marketed aqueous eyedrops at relatively lower dose; improved bioavailability; patent pending (US20200268648 A1) | [115] |
| Omega-3 EvoTears ® Omega | SFA (F6H8) | Improvement in clinical signs and subjective symptoms in patients with evaporative DED after 8 weeks. Currently marketed in Europe, Australia and New Zealand | [116] |
| Hydrocortisone, prednisolone, erythromycin, pimecrolimus,, a corticosteroid, ciprofloxacin | Squalane, with/without mineral oil | Vehicle beneficial for symptomatic relief in DED; high drug payload; potential to reduce dosing frequency; no penetration or efficacy studies performed; patent granted in 2019 (WO2017066429) | [117] |
| Suspensions | | | |
| Pilocarpine, dapiprazole, tetrahydrozoline | Vegetable oils, glycerol, mineral oil and white petrolatum | Improved therapeutic effect and reduced ocular adverse effects; improved shelf stability at ambient temperature; patent abandoned (US20100323978A1) | [118] |
| Phenylephrine | Sesame seed oil | Faster onset of action and higher therapeutic response than from high-dose viscous aqueous formulation; patent expired (US4623664A/US4705798A) | [68], [69], [119] |
| Vancomycin | Squalane | Improved drug stability at room temperature and 60° C. in comparison to an aqueous ointment; patent pending (WO2016196989 A1) | [80] |
| Self-emulsifying drug delivery systems | | | |
| Cyclosporine A Cyporin-N, T-sporin | Not disclosed | Improved clinical efficiency with faster onset of action than Restasis; currently marketed in South Korea for DED | [120] |
| Prednisolone, cortisone | Several oils and surfactants | Improved drug loading and solubilization; in vivo toxicity observed with several excipients; patent pending (US20220218599 A1) | [121] |
| Lutein | Isopropyl myristate, ethanol, triacetin and Tween 80 | Improved drug stability and drug release profile in vitro; formulation tolerability and toxicity not evaluated | [83] |
| Terconazole | Corn oil, PEG-6 esters, Tween 80 and Transcutol | Improved drug stability, rapid drug release; no conjunctival irritation in vitro; no in vivo studies performed | [81] |
| Econzole nitrate | Capmul ® MCM, Cremophor RH 40, Transcutol and hydroxypropylmethyl cellulose | Enhanced penetration; faster onset of action; acceptable in vitro and in vivo safety | [122] |
| Prednisolone | Linoleic acid, Cremophor RH 40 and propylene glycol | Improved ocular bioavailability; reduced precorneal drainage; significant improvement in clinical signs of uveitis in vivo | [123] |
| Econazole nitrate | S-protected thiolated Eudragit ® L100-55-BAK ion pair, Labrafil M 1944CS | Mucoadhesive; sustained drug release over 8 h; good in vitro release profile; no in vivo studies performed | [124] |

TABLE 1-continued

Non-aqueous vehicles used in ocular drug delivery systems.

| Drug (Tradename) | Vehicle | Study outcome | Ref. |
| --- | --- | --- | --- |
| Oleogels | | | |
| Dexamethasone; cyclosporine; triamcinolone; vancomycin | Soyabean oil, beeswax and gelator | Extended drug release; customisable release profile and oleogel texture | [125], [126] |

Priyanka Agarwal, Ilva D. Rupenthal, Non-aqueous formulations in topical ocular drug delivery—A paradigm shift?. Advance Drug Delivery Reviews Volume 198, 2023, 114867; https://doi.org/10.1016/j.addr.2023.114867

Cassie-Baxter state means the unwettable surface condition that results when, due to the hierarchical structure roughness (micro roughness covered with nano roughness) and angles of the solid surface, it is energetically more profitable (in a surface tension sense) for the liquid's molecules to adhere to one another than it is to fill in the valleys of the rough surface and thus actually touch the solid surface.

Surface tension means the elastic tendency of a fluid surface, caused by the polar cohesion of the molecules within the fluid and positively correlated with the polarity of the fluid's molecules (i.e., non-polar molecules result in fluids with the least surface tension), that makes a fluid acquire the least surface area possible.

Laplace pressure means the pressure difference between the inside and the outside of a curved surface such as the pressure difference caused by the surface tension of the interface between a liquid and a gas.

Mixture means the physical combination of two or more different substances which are mixed but are not combined chemically and includes being in the form of form of solutions, emulsions, suspensions, and colloids.

Emulsifier means a compound or substance at acts as a stabilizer for emulsions preventing the liquids from separating.

Emulsion means a mixture of two or more liquids that are normally immiscible such that the first liquid (the dispersed phase) is dispersed in the other, second liquid (the continuous phase) and includes reverse emulsions.

Excipient means a substance that serves as the vehicle or medium for a drug or other active substance and may itself be an active substance.

Sub-antibiotic means an amount or concentration of antibiotic agent that is below what is typically administered to kill or inhibit the growth of bacteria.

Medicament means a drug or preparation used for the prevention of disease or that promotes recovery from an injury, ailment, or disease.

Colloid means a mixture in which one substance consisting of microscopically dispersed insoluble particles is suspended throughout another substance.

Terpene means any of a class of hydrocarbons occurring widely in plants and animals built up from isoprene, a hydrocarbon consisting of five carbon atoms attached to eight hydrogen atoms (C5H8), including oxygenated and fatty acid derivatives of these hydrocarbons.

SUMMARY OF THE INVENTION

In a preferred embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron.

In another embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, and including that the medicament of the present invention's mixture is an anti-parasitical medicament.

In another embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, and including that the medicament of the present invention's mixture is a sub-antibiotic dose of a macrolide, or a avermectin, or a pyrethroid, or a benzoate, pimecrolimus or a milbemycin, or an anilide, or crotamiton, or lindane, or a pyrethrin, or a subantibiotic dose of azelaic acid, including any mixture of any of these medicaments with one another.

In another embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, and including that the arthropod of the present invention is a parasite of a mammal or a honey bee.

In another embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, and including that the medicament of the present invention's mixture is an anti-parasitical medicament and including that the medicament of the mixture of the present invention is used in the treatment of blepharitis, or dry eye disease, or meibomian gland dysfunction, or Athlete's Foot disease, or head lice infestation, or bed bug infestation, or tick infestation, or scabies, or impetigo, or acne rosacea.

In another preferred embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, including that the medicament of the present invention's mixture is an anti-parasitical medicament, and including that the medicament of the present invention's mixture contains an avermectin and contains tea tree oil to improve the solubility of the avermectin.

In another embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, including that the medicament of the present invention's mixture is an anti-parasitical medicament and including that the medicament of the mixture of the present invention is used in the treatment of blepharitis, or dry eye disease, or meibomian gland dysfunction, or Athlete's Foot disease, or head lice infestation, or bed bug infestation, or tick infestation, or scabies, or impetigo, or acne rosacea, including that the medicament of the mixture of the present invention is used in the treatment of dry eye disease or meibomian gland dysfunction and including that the mixture also includes cyclosporin, pimecrolimus or Cyporin-N, or T-sporin, or a corticosteroid, or cyclosporin A, including any mixture of any of these medicaments with one another, to improve the treatment of the disease.

In another embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, including that the mixture of the present invention does not include water and contains an emulsion.

In another embodiment, the present invention provides a method of introducing medicaments into/onto the body of an arthropod that has cuticular, Cassie-Baxter state, air-filled plastron by mixing, the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, including that the mixture of the present invention does not include water and contains a colloid.

In another embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, including that the mixture of the present invention does not include water and contains a colloid and hyaluronic acid.

In another embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, including that the medicament of the present invention's mixture is an anti-parasitical medicament and including that the medicament of the mixture of the present invention is used in the treatment of blepharitis, or dry eye disease, or meibomian gland dysfunction, or Athlete's Foot disease, or head lice infestation, or bed bug infestation, or tick infestation, or scabies, or impetigo, or acne rosacea, including that, when the medicament of the mixture of the present invention is used in the treatment of Athlete's Foot disease or nail fungus disease (Toenail onychomycosis), the mixture also contains tea tree oil, or triazoles, or corticosteroids, or imidazoles, including any mixture of any of these medicaments with one another, to improve the treatment of the disease.

In another preferred embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, including that the medicament of the present invention's mixture is an anti-parasitical medicament and including that the medicament of the mixture of the present invention is used in the treatment of blepharitis, or dry eye disease, or meibomian gland dysfunction, or Athlete's Foot disease, or head lice infestation, or bed bug infestation, or tick infestation, or scabies, or impetigo, or acne rosacea, and including that, when the medicament of the mixture of the present invention is used in the treatment of blepharitis, the mixture also contains erythromycin, or pimecrolimus, or a corticosteroid, or ciprofloxacin, or vancomycin, including any mixture of any of these medicaments with one another to improve the treatment of the disease.

In another embodiment, the present invention provides a method of introducing medicaments into/onto the body of an arthropod that has cuticular, Cassie-Baxter state, air-filled plastron by mixing the medicament with a low molecular weight non-polar chemical excipient, not including xylene and perfluorohexyloctane. Due to the mixture having a sufficiently low surface tension and sufficiently small molecular size such that it is incapable of forming a Cassie-Baxter state with the arthropod plastron, the medicament mixture is able to reach and touch the body of the mite when the mixture passes through/penetrates the plastron, and including that the arthropod of the present invention is an *Acari*, a *Heteroptera*, or *Anoplura* arthropod.

I claim:

1. A method of introducing medicaments into/onto the body of an arthropod that has cuticular, Cassie-Baxter state, air-filled plastron, the method comprising: mixing the medicament with a low molecular weight non-polar chemical excipient having a sufficiently low surface tension and sufficiently small molecular size such that it is incapable of forming a Cassie-Baxter state with the arthropod plastron, introducing/applying/interfacing/touching the mixture onto the arthropod, the mixture having a sufficiently low surface tension and sufficiently small molecular size such, that it is incapable of forming a Cassie-Baxter state with the arthropod plastron in order to wet/touch the body of the arthropod with the medicament.

2. The method of claim 1, wherein the medicament of the mixture is an anti-parasitical medicament, not including a pyrethroid.

3. The method of claim 2, wherein the medicament is selected from the group consisting of a sub-antibiotic dose of a macrolide, an avermectin, a benzoate, pimecrolimus, a milbemycin, an anilide, crotamiton, lindane, and a sub-antibiotic dose of azelaic acid, including any mixture of any of these medicaments with one another.

4. The method of claim 1, wherein the arthropod is a parasite of a host selected from the group consisting of a mammal, and a honey bee.

5. The method of claim 2, wherein the medicament of the mixture is used in the treatment of a disease selected from the group consisting of blepharitis, dry eye disease, meibomian gland dysfunction, Athlete's Foot disease, head lice infestation, bed bug infestation, tick infestation, scabies, impetigo, and acne rosacea.

6. The method of claim 2, wherein the mixture contains an avermectin and contains tea tree oil to improve the solubility of the avermectin.

7. The method of claim 5, wherein the disease is selected from the group consisting of dry eye disease and meibomian gland dysfunction and the mixture also includes a medicament selected from the group consisting of cyclosporin, pimecrolimus, nanoemulsified cyclosporin-A, a corticosteroid and cyclosporin A, including any mixture of any of these medicaments with one another, to improve the treatment of the disease.

8. The mixture of claim 1, wherein the mixture does not include water and contains an emulsion.

9. The mixture of claim 1, wherein the mixture does not include water and contains a colloid.

10. The mixture of claim 9, wherein the mixture contains hyaluronic acid.

11. The method of claim 5, wherein the wherein the disease is selected from the group consisting of Athlete's Foot disease and nail fungus disease and the mixture also contains medicament selected from the group consisting of tea tree oil, triazoles, corticosteroids, and imidazoles, including any mixture of any of these medicaments with one another, to improve the treatment of the disease.

12. The method of claim 5, wherein the disease is blepharitis and the mixture also contains medicament selected from the group consisting of erythromycin, pimecrolimus, a corticosteroid, ciprofloxacin, and vancomycin, including any mixture of any of these medicaments with one another, to improve the treatment of the disease.

13. The method of claim 1, wherein the arthropod is selected from the group consisting of: *Acari; Heteroptera*; and, *Anoplura.*

14. The method of claim 1, wherein the excipient is selected from the group consisting of a semifluorinated alkane, a terpene, a dimethicone, or any mixture of any of these chemicals.

* * * * *